(12) United States Patent
Heresco-Levy et al.

(10) Patent No.: US 9,789,093 B2
(45) Date of Patent: Oct. 17, 2017

(54) DOSAGE REGIMEN, MEDICATION DISPENSING PACKAGE AND USES THEREOF FOR THE TREATMENT OF MAJOR DEPRESSIVE DISORDER

(75) Inventors: Uriel Heresco-Levy, Jerusalem (IL); Daniel Javitt, Bardonia, NY (US)

(73) Assignee: Serotech, LLC, Wilmington, DE (US)

(*) Notice: Subject to any disclaimer, the term of this patent is extended or adjusted under 35 U.S.C. 154(b) by 0 days.

(21) Appl. No.: 13/982,460

(22) PCT Filed: Jan. 30, 2012

(86) PCT No.: PCT/IL2012/050034
§ 371 (c)(1),
(2), (4) Date: Sep. 29, 2013

(87) PCT Pub. No.: WO2012/104852
PCT Pub. Date: Aug. 9, 2012

(65) Prior Publication Data
US 2014/0018349 A1    Jan. 16, 2014

Related U.S. Application Data

(60) Provisional application No. 61/437,700, filed on Jan. 31, 2011, provisional application No. 61/494,907, filed on Jun. 9, 2011.

(51) Int. Cl.

| | |
|---|---|
| *A61K 31/198* | (2006.01) |
| *A61K 31/42* | (2006.01) |
| *A61K 31/496* | (2006.01) |
| *A61K 31/519* | (2006.01) |
| *A61K 31/5513* | (2006.01) |
| *A61K 45/06* | (2006.01) |
| *A61K 31/137* | (2006.01) |
| *A61K 31/551* | (2006.01) |
| *A61K 31/554* | (2006.01) |

(52) U.S. Cl.
CPC ............ *A61K 31/42* (2013.01); *A61K 31/137* (2013.01); *A61K 31/496* (2013.01); *A61K 31/519* (2013.01); *A61K 31/551* (2013.01); *A61K 31/554* (2013.01); *A61K 31/5513* (2013.01); *A61K 45/06* (2013.01)

(58) Field of Classification Search
CPC .................................................. A61K 31/198
USPC ....................................................... 514/596
See application file for complete search history.

(56) References Cited

U.S. PATENT DOCUMENTS

| | | | |
|---|---|---|---|
| 6,228,875 B1 * | 5/2001 | Tsai et al. ..................... 514/380 |
| 2005/0112198 A1 * | 5/2005 | Challapalli et al. .......... 424/464 |
| 2009/0209638 A1 * | 8/2009 | Birznieks et al. ............ 514/469 |
| 2010/0216430 A1 | 8/2010 | Barlow et al. |

FOREIGN PATENT DOCUMENTS

| | | | | |
|---|---|---|---|---|
| EP | 0 387 867 B1 * | 5/1993 | ............. A61K 31/42 |
| NL | WO 2010/070061 A1 * | 6/2010 | ........... A61K 31/496 |

OTHER PUBLICATIONS

Y Ji, et al. Clinical Pharmacology & Therapeutics | vol. 89 No. 1 | Jan. 2011: advance online publication Nov. 24, 2010. doi:10.1038/clpt.2010.250.*

Heresco-Levy et al, in Journal of Affective Disorders 93 (2006) 239-243.*

Sumiyoshi, et al., International Journal of Neuropsychopharmacology (2004), 7, 1-8.*

* cited by examiner

*Primary Examiner* — San-Ming Hui
(74) *Attorney, Agent, or Firm* — Neifeld IP Law

(57) ABSTRACT

This invention provides an oral dosage regimen for the treatment of depression, a pharmaceutically acceptable medication dispensing package containing multiple dosage units of medicaments comprising an oral dosage regimen of D-cycloserine for the treatment of depression, a pharmaceutical composition comprising D-cycloserine formulated for oral administration providing a dosage of 1000 mg/day alone or in combination with antidepressant agents and uses thereof.

12 Claims, No Drawings

DOSAGE REGIMEN, MEDICATION DISPENSING PACKAGE AND USES THEREOF FOR THE TREATMENT OF MAJOR DEPRESSIVE DISORDER

CROSS REFERENCE TO RELATED APPLICATIONS

This application is a 371 national stage entry of PCT/IL2012/050034 filed on Jan. 30, 2012, which claims benefit of U.S. 61/437,700, filed on Jan. 31, 2011, and U.S. 61/494,907, filed on Jun. 9, 2011. The above-referenced applications are incorporated by reference in its entirety.

BACKGROUND OF THE INVENTION

Major depression is a clinical syndrome that includes a persistent sad mood or loss of interest in activities, which persists for at least two weeks in the absence of treatment. Symptoms of major depression are typically measured using rating scales such as the Hamilton Depression Rating Scale (HAM-D) or the Beck Depression Inventory (BDI). In addition to including symptoms relevant to depressed mood, the HAM-D also contains symptoms sensitive to psychosis, including items for guilt, depersonalization/derealization and paranoia. Major to depression may also be associated with symptoms of anxiety, which may be measured with rating scales such as the Hamilton Rating Scale for Anxiety (HAM-A). Depressive disorders are divided in major depression (MDD) and bipolar depression (BPD). Major depression may also occur with and without melancholic features. In addition, depressive symptoms may occur in the context of anxiety disorders such as generalized anxiety disorder, dissociative disorders, personality disorders or adjustment disorders with depressed mood (DSM-IV).

Current treatments for major depression consist primarily of older antidepressants, such as monoamine oxidase inhibitors (MAOI) and tricyclic antidepressants (TCAs) (e.g. imipramine, amitryptiline, desipramine, clomipramine) that were first developed in the 1960's, and newer agents such as tetracyclic antidepressants (TeCAs) (e.g., mianserin, mirtazapine), serotonin (SSRI) and serotonin/norephinephrine (SNRI) reuptake inhibitors (e.g., fluoxetine, fluvoxamine, paroxetine, citalopram, escitalopram, duloxetine, venlafaxine, dapoxetine, indalpine, valzodone). MAOIs and TCAs are considered "broader spectrum" agents than SSRIs/SNARIs that were developed subsequently.

However, current treatment approaches have severe limitations. Only 60-65% of patients respond to the initial regimen and among those responding, less than half either reach remission or become symptom-free. Individuals not responding to a first course of antidepressant treatment are often switched to a different drug, with results that are generally modest and incremental.

Antipsychotics may be divided into typical (e.g. chlorpromazine, haloperidol) vs. atypical (e.g. risperidone, olanzapine, quetiapine, aripiprazole, clozapine) based upon receptor binding, preclinical effects and side effect profile. Several antipsychotic agents, including quetiapine, risperidone, olanzapine and aripiprazole are also indicated for treatment of depression in both major depressive and bipolar disorders.

TCAs and SSRIs show approximately equal efficacy in treatment of non-melanchoic forms of depression, suggesting overlapping but differentiable mechanisms of action. TCAs as a group show limited antipsychotic activity, alone or in combination with antipsychotics, but may be effective in treating persistent depressive symptoms in stabilized schizophrenia patients. TCAs have been shown to worsen psychosis in acutely decompensated schizophrenia patients, but to be relatively without effect on psychosis during the chronic phase of illness. In contrast, SSRIs and TeCAs may improve psychotic symptoms in addition to treatment of depression in refractory schizophrenia, suggesting a differential mechanism of action and mild antipsychotic potency.

Treatment-refractory depression refers to a form of depression that responds poorly to currently available treatments (e.g., http://www.nimh.nih.gov/trials/practical/stard/index.shtml June 2011) and which may have different underlying etiopathological mechanisms compared with other forms of depression. Combinations of antidepressants have not been shown to be superior to monotherapy for refractory depression and typically increase risk of side effects and are not recommended.

Risk for suicide is significantly increased in depressive disorders, but may respond differentially to medication versus depressive symptoms as a whole. When suicide occurs, it is often accompanied by feelings of worthlessness or inappropriate guilt, as well as recurrent thoughts of death or suicidial ideation and guilt is an accepted proxy for suicide. While the risk of suicide increases in subjects with a depressive disorder, medications used to date to typically treat depressive disorders paradoxically increase suicidal tendencies.

Most current theories of depression focus on serotonergic and/or noradrenergic brain systems. Glutamate is an alternative brain neurotransmitter that has been studied to a limited degree in relationship to depression or other affective disorders. Glutamate binds to several receptor types including N-methyl-D-aspartate type glutamate receptors (NMDAR). NMDAR contain multiple binding sites including an agonist site for glutamate and an allosteric modulatory site (aka glycineB receptor, strychnine-insensitive glycine receptor) sensitive to the endogenous brain amino acids glycine and D-serine. Agonists at the glycine site increase NMDAR activation in response to glutamate while antagonists decrease NMDAR activation.

Functional agonists and antagonists at the glycine site can be identified using well-validated electrophysiological assays such as modulation of NMDA-receptor mediated responses to NMDA glutamate-site agonists, or radioreceptor assays, such as modulation of binding to the NMDA PCP-receptor channel binding site. Glycine site agonists and antagonists can also be distinguished based upon both electrophysiology and receptor binding from compounds such as phencyclidine (PCP) or ketamine that bind to the channel site (aka PCP receptor, uncompetitive antagonist site) of the NMDAR. Effective agonists and antagonists may be identified, for example, as compounds with <100 nM affinity for their target and >10-fold selectivity vs. other relevant targets. Partial agonists are defined as compounds that have reduced efficacy for inducing conformational change in receptors (typically 40-80%) relative to full agonists, and which may induce agonist effects at low dose but antagonist effects at high dose.

Relatively few studies have investigated glutamate- or NMDAR-related measures in depression. To the extent that it has been studied, it has been suggested that depression is associated with reduced NMDAR function (e.g. Frye et al., 2007). Sumiyoshi et al. (2004) found to no difference in plasma glycine levels relative to controls. In contrast, other studies have linked high glycine levels to poor response to SSRIs, possibly in association with abnormalities in the glycine hydroxylase (decarboxylating) (aka decarboxylase, GLDC) gene suggesting that treatment refractory depression may constitute an etiologically distinct form of the disorder (Ji et al., 2011). Depression may be modeled in rodents using assays such as learned helplessness, forced swim or tail suspension tests. There are at present no animal models specifically sensitive to treatment refractory depression. Elevated glycine levels are also reported in relapsing mania. For example, Hoekstra et al., 2006 reported mean plasma levels of 283.3±102.7 for manic patients vs. a mean of 224.0±51.5 for controls (p=0.02).

Recently, the non-competitive NMDAR antagonist ketamine has also been shown to have antidepressant effects in humans when tested in individuals with treatment-resistant depression. The compound shows similar effects in both unipolar and bipolar depression. Other non-competitive NMDAR antagonists such as MK-801 also show antidepressant effects in animal models. However, antidepressant effects induced by ketamine are associated with exacerbation of psychosis, which greatly reduces their utility in clinical situations.

A recent, double-blind, randomized, placebo-controlled clinical trial evaluating the NMDAR-2B subunit-selective antagonist CP-101,606 found that this agent also induced significant and relatively rapid antidepressant effects in patients with treatment-resistant MDD. As with ketamine, however, CP-101,606 was used by intermittent IV infusion, limiting its clinical utility. Moreover, as with ketamine, significant dissociative effects emerged during CP-101,6060 infusion. Other NMDAR antagonists, such as memantine, have not shown beneficial clinical results. Based upon the lack of efficacy of memantine, it has been suggested that intravenous infusion may be critical for effect anti-depressive treatment.

D-cycloserine is a compound currently approved for treatment of tuberculosis (TB). Psychotropic effects of cycloserine were noted in the late 1950's in patients being treated for TB. In an initial report, effects of cycloserine were noted on symptoms such as anorexia, asthenia and insominia. However, no formal psychiatric diagnoses were made. Furthermore, cycloserine was recommended primarily for treatments of tension and insomnia, as opposed to depression.

Formal further studies with D-cycloserine were not pursued until the 1980's when it was observed that D-cycloserine functions as a partial agonist (mixed agonist/antagonist) at the glycine binding site of the NMDAR, with agonist effects predominating at low dose and antagonist effects predominating at high dose. As compared to glycine, D-cycloserine shows approximately 50% efficacy in stimulating NMDA receptors when used at maximal concentration.

Because of its ability to bind to NMDAR and because of theories linking NMDAR to schizophrenia, D-cycloserine has been studied in treatment resistant schizophrenia. At low doses, D-cycloserine has been found to produce beneficial effects in some but not all studies, and may exacerbate symptoms in individuals receiving clozapine. Furthermore, at higher doses (>250 mg), however, D-cycloserine exacerbates psychosis and so according to package label insert is contra-indicated in schizophrenia, depression and anxiety disorders.

D-cycloserine has also been assessed in the treatment of anxiety disorders, PTSD and enhancement of learning and memory at doses of 50-500 mg, with the goal primarily of enhancing NMDAR function. In addition, use of D-cycloserine has been claimed for enhancement of cognition at doses of up to 100 mg and for treatment of a wide variety of neuropsychiatric disorders at doses of up to 500 mg. It has also been taught that D-cycloserine may be useful in augmenting cognition in Parkinsons disease.

In both anxiety and schizophrenia studies, it has been noted that effects of D-cycloserine may decrease over time during repeated treatment, leading some to advocate use of weekly, rather than daily, D-cycloserine. When used as augmentation of behavior therapy for anxiety, D-cycloserine is used episodically in combination with behavioral therapy sessions.

Research with D-cycloserine in preclinical models has also not suggested its usefulness at high dose in treatment of depression. Partial agonists of NMDAR, in particular 1-aminocyclopropanecarboxylic acid (ACPC) have been reported to have efficacy in animal models, but have not yet been tested in human studies. When used in these models, D-cycloserine was noted to have inconsistent effects and to be less effective than either ACPC or imipramine. Furthermore, effects were only observed at the lowest dose tested, arguing away from high dose treatment in humans. In animal depression models, tolerance over weeks has also been observed, arguing against sustained long term use.

D-cycloserine reported for use at a dose of 250 mg/day was found to be without significant effect on symptoms of major depression and moreover, commonly available prescribing information states that cycloserine use is contraindicated in individuals with a history of epilepsy, depression, severe anxiety, or psychosis (Lilly. Seromycin (cycloserine) capsules prescribing information. Indianapolis, Ind.; 2005 Apr. 28).

SUMMARY OF THE INVENTION

In one embodiment, this invention provides an oral dosage regimen consisting essentially of two active ingredients, wherein a first of said two active ingredients is D-cycloserine at a dosage of from about 500 mg/day-1200 mg/day and wherein a second of said two active ingredients is a therapeutic agent for the treatment of depression, for reduction of the incidence of suicide or for the treatment of suicide ideation in a subject or population, or a combination thereof.

In some embodiments, the second therapeutic agent comprises a tetracyclic antidepressant (TeCA), selective serotonin reuptake inhibitor (SSRI), a serotonin/norephinephrine reuptake inhibitor (SNRI) or a combination thereof.

In some embodiments, the second therapeutic agent is an antipsychotic agent, which antipsychotic agent is also approved for the treatment of depression In some embodiments, the antipsychotic agent is selected from the group consisting of quetiapine, risperidone, olanzapine and aripiprazole In some embodiments, the second therapeutic agent is provided at a subtherapeutic dose, if the second therapeutic agent were provided alone.

In some embodiments, the two active ingredients are provided in a single pharmaceutical composition.

In some embodiments, this invention provides a method for treating depression in a subject in need thereof, said method comprising providing said subject with an oral dosage regimen as herein described.

In some embodiments, the subject has previously received treatment with an anti-depressant agent.

In some embodiments, the said anti-depressant agent is ketamine. In some embodiments, the anti-depressant agent is an anti-NMDA agent.

In some embodiments, the patients have pretreatment plasma levels ≥300 µM glycine. In some embodiments, the subject possesses a polymorphism for a GLDC allele. In some embodiments, the subject possesses a polymorphism at locus rs10975641, rs11789777, rs10975734, rs1658957, rs11612037, rs7485577, rs2988418, rs1755615 or rs12004478 of the GLDC gene.

In some embodiments, the subject suffers from mania, or in some embodiments, the subject suffers from bipolar disorder. In some embodiments, the invention provides a method for reducing the incidence or treating suicide or suicide ideation in a subject or population in need thereof, the method comprising providing the subject with an oral dosage regimen as herein described.

In some embodiments, the invention provides an oral dosage regimen for the treatment of depression, said dosage regimen comprising:
- a first dosage of 50-300 mg/day of D-cycloserine for from 1 to 5 days, followed by:
- a second dosage of 300-600 mg/day of D-cycloserine for from 5 to 20 days, followed by:
- a third dosage of from 600-800 mg/day of D-cycloserine for from 21 days to 28 days, followed by:
- a fourth dosage of from 800-1200 mg/day of D-cycloserine for from day 29-43.

In some embodiments, the invention provides a pharmaceutically acceptable medication dispensing package containing multiple dosage units of medicaments comprising an oral dosage regimen of D-cycloserine for the treatment of depression, in a manner that provides a complex regimen of said medicaments for consumption by a patient over the period of time necessary to treat depression in a subject, said package including first pills comprising 50-300 mg/day of D-cycloserine to be administered for from 1 to 5 days, followed by second pills comprising 300-600 mg/day of D-cycloserine to be administered for from 5 to 20 days, followed by third pills comprising from 600-800 mg/day of D-cycloserine to be administered for from 21 days to 28 days, followed by fourth pills comprising 800-1200 mg/day of D-cycloserine for from day 29-43 days,
wherein the package retains and presents said medicaments at separate locations identified by visibly discernible indicia identifying the administration schedule for the medicaments contained respectively, therein.

In some embodiments, the invention provides a method for treating depression in a subject, said method comprising orally administering D-cycloserine to a subject, wherein said D-cycloserine is administered in a dosage regimen as follows:
- a first dosage of 50-300 mg/day of D-cycloserine for from 1 to 5 days, followed by:
- a second dosage of 300-600 mg/day of D-cycloserine for from 5 to 20 days, followed by:
- a third dosage of from 600-800 mg/day of D-cycloserine for from 21 days to 28 days, followed by:
- a fourth dosage of from 800-1200 mg/day of D-cycloserine for from day 29-43.

In some embodiments, the invention provides for the use of D-cycloserine in the preparation of a medicament or kit, formulated to provide a dosage regimen as follows
- a first dosage of 50-300 mg/day of D-cycloserine for from 1 to 5 days, followed by:
- a second dosage of 300-600 mg/day of D-cycloserine for from 5 to 20 days, followed by:
- a third dosage of from 600-800 mg/day of D-cycloserine for from 21 days to 28 days, followed by:
- a fourth dosage of from 800-1200 mg/day of D-cycloserine for from 29 days to 43 days; for treating depression in a subject, wherein said D-cycloserine is formulated for oral administration to a subject.

In some embodiments, the invention provides a pharmaceutical composition comprising D-cycloserine formulated for oral administration providing a dosage of 1000 mg/day. In some embodiments, the invention provides a pharmaceutical composition comprising D-cycloserine formulated for oral administration providing a dosage of between 775-2000 mg/day.

In some embodiments, the invention provides a method for the treatment of depression in a subject, said method comprising orally administering 1000 mg/day of D-cycloserine to a subject in need thereof, wherein said subject has first been administered D-cycloserine at dosage of between 50-500 mg/day of D-cycloserine for from 7 days to 21 says prior to administering said 1000 mg/day or D-cycloserine. In some embodiments, the invention provides a method for the treatment of depression in a subject, said method comprising orally administering between 775-2000 mg/day of D-cycloserine to a subject in need thereof, wherein said subject has first been administered D-cycloserine at dosage of between 50-500 mg/day of D-cycloserine for from 7 days to 21 says prior to administering said 775-2000 mg/day or D-cycloserine.:

In other embodiments, the invention provides for the use of D-cycloserine in the preparation of a medicament formulated for oral administration at a dosage of 1000 mg/day for the treatment of depression in a subject in need thereof. In other embodiments, the invention provides for the use of D-cycloserine in the preparation of a medicament formulated for oral administration at a dosage of 775-2000 mg/day for the treatment of depression in a subject in need thereof.

In other embodiments, the invention provides a method for treating neuropsychiatric disorders associated with elevated plasma glycine levels is a subject, said method comprising the step of administering an NMDAR glycine-site antagonist to said subject. In some embodiments, the subject suffers from treatment-refractory depression or relapsing mania and in some embodiments, the subject exhibits a pretreatment plasma level of >300 µM glycine.

In some embodiments, the invention provides a method for reducing the incidence or treating suicide or suicide ideation in a subject or population, said method comprising orally administering D-cycloserine to a subject, wherein said D-cycloserine is administered in a dosage regimen as follows
- a first dosage of 50-300 mg/day of D-cycloserine for from 1 to 5 days, followed by:
- a second dosage of 300-600 mg/day of D-cycloserine for from 5 to 20 days, followed by:
- a third dosage of from 600-800 mg/day of D-cycloserine for from 21 days to 28 days, followed by:
- a fourth dosage of from 800-1200 mg/day of D-cycloserine for from 29 days to 43 days.

In some embodiments, the invention provides for the use of D-cycloserine for the preparation of a medicament/kit formulated to provide a dosage regimen as follows
- a first dosage of 50-300 mg/day of D-cycloserine for from 1 to 5 days, followed by:
- a second dosage of 300-600 mg/day of D-cycloserine for from 5 to 20 days, followed by:
- a third dosage of from 600-800 mg/day of D-cycloserine for from 21 days to 28 days, followed by:
- a fourth dosage of from 800-1200 mg/day of D-cycloserine for from 29 days to 43 days.
for reducing the incidence or treating suicide or suicide ideation in a subject or population, wherein said D-cycloserine is formulated for oral administration.

DETAILED DESCRIPTION OF THE INVENTION

This invention provides, in some embodiments, oral dosage regimens, which are useful in the treatment of depression in a subject in need thereof, or in the reduction of the incidence or treatment of suicide or suicide ideation in a subject or population in need thereof.

In some embodiments, the invention provides an oral dosage regimen consisting essentially of two active ingredients, wherein a first of said two active ingredients is D-cycloserine at a dosage of from about 500 mg/day-1200 mg/day and wherein a second of said two active ingredients is a therapeutic agent for the treatment of depression, for reduction of the incidence of suicide or for the treatment of suicide ideation in a subject or population, or a combination thereof.

In some embodiments, the second therapeutic agent comprises a tetracyclic antidepressant (TeCA), selective serotonin reuptake inhibitor (SSRI), a serotonin/norephinephrine reuptake inhibitor (SNRI) or a combination thereof.

In some embodiments, the second therapeutic agent is an antipsychotic agent, which antipsychotic agent is also approved for the treatment of depression In some embodiments, the antipsychotic agent is selected from the group consisting of to quetiapine, risperidone, olanzapine and aripiprazole In some embodiments, the two active ingredients are provided in a single pharmaceutical composition, and in some embodiments, the invention contemplates a kit or combined dispenser packet containing each of the two active ingredients.

It is to be understood that the invention contemplates the co-administration of either of the two active ingredients to a subject, whether such administration is combined in a single formulation or in separate formulations and whether such administration is coincident or staggered.

In some embodiments, this invention provides a method for treating depression in a subject in need thereof, said method comprising providing said subject with an oral dosage regimen as herein described.

In some embodiments, the subject suffers from mania, or in some embodiments, the subject suffers from bipolar disorder. In some embodiments, the invention provides a method for reducing the incidence or treating suicide or suicide ideation in a subject or population in need thereof, the method comprising providing the subject with an oral dosage regimen as herein described.

This invention provides, in some embodiments, for staggered dosage regimens, medication dispensing packages for providing the same and methods of use thereof for the treatment of depression in a subject, whereby a dosage of up to 2000 mg/of D-cycloserine is safely provided to a subject resulting in effective treatment of depression and the without promoting psychosis in the subject.

In one embodiment, this invention provides an oral dosage regimen for the treatment of depression, said dosage regimen comprising:
 a first dosage of 50-300 mg/day of D-cycloserine for from 1 to 5 days, followed by:
 a second dosage of 300-600 mg/day of D-cycloserine for from 5 to 20 days, followed by:
 a third dosage of from 600-800 mg/day of D-cycloserine for from 21 days to 28 days, followed by:
 a fourth dosage of from 800-1200 mg/day of D-cycloserine for from 29 days to 43 days.

In some embodiments, the first dosage comprises 250 mg/day of D-cycloserine for 3 days, in some embodiments, the second dosage comprises 500 mg/day of D-cycloserine for 18 days, in some embodiments, the third dosage comprises 750 mg/day of D-cycloserine for 7 days, in some embodiments, the fourth dosage comprises 1000 mg/day of D-cycloserine for 18 days and in some embodiments, the invention provides for the administration of the combined dosage regimen according to this aspect. In some embodiments, the fourth dosage comprises between 775-2000 mg/day of D-cycloserine In some embodiments, the first dosage comprises 250 mg/day of D-cycloserine from day 0-7, in some embodiments, the second dosage comprises 500 mg/day of D-cycloserine from day 12-20, in some embodiments, the third dosage comprises 750 mg/day of D-cycloserine from day 18-25 days, in some embodiments, the fourth dosage comprises 1000 mg/day of D-cycloserine from day 25-35 days and in some embodiments, the invention provides for the administration of the combined dosage regimen according to this aspect. In some embodiments, the fourth dosage comprises between 775-2000 mg/day of D-cycloserine from day 30-40. In some embodiments, the first dosage comprises 250 mg/day of D-cycloserine from day 0-7, or any number of days from within such range, such as, for example, days 1-3, 1-4, 1-5, etc. In some embodiments, the second dosage comprises 500 mg/day of D-cycloserine from day 4-21, or any number of days from within such range, such as, for example, days 4-16, 5-21, 7-21, etc. In some embodiments, the third dosage comprises 750 mg/day of D-cycloserine from day 20-35 days, or any number of days from within such range, such as, for example, days 22-28, 21-30, 22-35, etc. In some embodiments, the fourth dosage comprises 1000 mg/day of D-cycloserine from day 36-50 days or any number of days from within such range, such as, for example, days 29-42, 33-50, 31-45, etc. In some embodiments, the invention provides for the administration of the combined dosage regimen according to this aspect.

Surprisingly, the Inventors have found herein that higher dosages of D-cycloserine can be significantly well tolerated, treating depression without any signs of developing psychosis in the subject, when D-cycloserine is combined with an antidepressant agent, especially when the dosage treatment schedule is increased over time in a relatively slow and fixed manner. Furthermore, the combination of D-cycloserine plus an anti-depressant is more effective than treatment with anti-depressant alone.

In some embodiments, the dosage regimens herein described provide for a therapeutically effective amount of D-cycloserine, in accordance with the regimens as herein described, providing an effective therapy for depression.

In some embodiments, reference to an "effective" amount or a "therapeutically effective amount" of D-cycloserine or other therapeutic agents referenced herein, it is meant a nontoxic but sufficient amount of the same to provide the desired effect. In a combination therapy of the present invention, an "effective amount" of one component of the combination is to the amount of that compound that is effective to provide the desired effect when used in combination with the other components of the combination. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual.

D-cycloserine, or DCS, refers to the chemical D-cycloserine (CA Index Name: 3-Isoxazolidinone, 4-amino-, (4R)-(9CI); CAS Registry No. 68-41-7), or pharmaceutically acceptable salts thereof. DCS is an FDA (United States Food and Drug Administration)-approved drug for treatment of tuberculosis, and is sold by Eli Lilly and Company under the trade name Seromycin®. DCS is a structural analog of D-alanine, and is a broad-spectrum antibiotic produced by some strains of *Streptomyces orchidaceus* and *S. garphalus*.

Indicia is provided and disposed adjacent the columns and rows for displaying common days and successive weeks. Thus, the package provides for a titration schedule which prevents adverse events as a result of mis-dosing. As a result, the package in accordance with the present invention provides for a safer and accordingly more beneficial method for enabling compliance with the regimen.

In some embodiments, the invention provides a regimen further comprising administering a second therapeutic agent for the treatment of depression or for the reduction of the incidence or treatment of suicide or suicide ideation in a subject or population in need thereof.

In some embodiments, the second therapeutic agent comprises a tetracyclic antidepressant (TeCA), selective serotonin reuptake inhibitor (SSRI), a serotonin/norephinephrine reuptake inhibitor (SNRI), an antipsychotic approved for treatment of depression or a combination thereof.

In some embodiments, the second therapeutic agent may comprise any agent as described and/or exemplified herein, for example, the second therapeutic agent may comprise antidepresseants, such as monoamine oxidase inhibitors (MAOI), TCAs such as, but not limited to imipramine, amitryptiline, desipramine, clomipramine, TeCAs such as mianserin, mirtazapine, serotonin (SSRI) and serotonin/norephinephrine (SNRI) reuptake inhibitors, such as fluoxetine, fluvoxamine, paroxetine, citalopram, escitalopram, duloxetine, venlafaxine and others, as will be appreciated by the skilled artisan.

In some embodiments, the regimen comprises administering a second therapeutic agent which is an anti-depressant, and said dosage is in accordance with standard prescribing guidelines.

In some embodiments, the regimen comprises a second therapeutic agent which is a psychotropic medication.

In some embodiments, the regimen comprises a second therapeutic agent which is venlafaxine, and in some embodiments, the venlafaxine is at a dosage of 25-500 mg.

In some embodiments, the regimen comprises a second therapeutic agent which is quetiapine, and in some embodiments, the quetiapin is at a dosage of 50-1000 mg.

In some embodiments, the regimen comprises D-cycloserine at a dosage of between 500-1200 mg and an antidepressant as herein described, where such regimen is particularly suitable for a patient previously receiving D-cyloserine alone at a dosage of less than 250 mg.

In some embodiments, the regimen includes a second therapeutic agent, which is an anti-anxiolytic, or a mood stabilizer.

In some embodiments, the anti-anxiolytic includes, inter alia, SSRI's, Atarax, Benadryl, azaspirones, benzodiazepines, such as Ativan, Centrax, Dalmane, Klonopin, Librium, Paxipam, Restoril, Serax, Tranxene, Valium, Xanax, beta blockers, such as Inderal, Tenormin and others as will be appreciated by the skilled artisan.

In some embodiments, the mood stabilizers may comprise lithium, valproic acid, carbamazepine, Eskalith, Lithium Carbonate, Lithonate, Depakote, Divalproex Sodium, Gabatril, Tiagabine, Zyprexa, Olanzapine and others, as will be appreciated by the skilled artisan.

In some embodiments, the regimen comprises administering a second therapeutic agent at a dosage which is considered to be suboptimal for treating depression in said subject when treating said subject with said second therapeutic agent alone. In some embodiments, such administration of the second therapeutic agent may be titrated downward, for example, as the dosage of D-cycloserine is increased in a subject, the dosage of the second therapeutic agent can be diminished gradually, over time. In another embodiment, the invention contemplates reaching maximal treatment levels of both D-cycloserine initially followed by gradual reduction of the second therapeutic agent.

In some embodiments, the invention provides a pharmaceutically acceptable medication dispensing package containing multiple dosage units of medicaments comprising an oral dosage regimen of D-cycloserine for the treatment of depression, in a manner that provides a complex regimen of said medicaments for consumption by a patient over the period of time necessary to treat depression in a subject, said package including first pills, capsules or other oral dosage forms comprising 50-300 mg/day of D-cycloserine to be administered for from 1 to 5 days, followed by second pills, capsules or other oral dosage forms comprising 300-600 mg/day of D-cycloserine to be administered for from 5 to 20 days, followed by third pills, capsules or other oral dosage forms comprising from 600-800 mg/day of D-cycloserine to be administered for from 21 days to 28 days, followed by fourth pills, capsules or other oral dosage forms comprising 800-1200 mg/day of D-cycloserine for from day 29-43 days, wherein the package retains and presents said medicaments at separate locations identified by visibly discernible indicia identifying the administration schedule for the medicaments contained respectively, therein.

In some embodiments, the pharmaceutically acceptable medication dispensing package specifically contains first pills, capsules or other oral dosage forms comprising a dosage of 250 mg/day of D-cycloserine. In some embodiments, the pharmaceutically acceptable medication dispensing package specifically contains second pills, capsules or other oral dosage forms comprising a dosage of 500 mg/day of D-cycloserine for 18 days. In some embodiments, the pharmaceutically acceptable medication dispensing package specifically contains third pills, capsules or other oral dosage forms comprising a dosage of 750 mg/day of D-cycloserine for 7 days. In some embodiments, the pharmaceutically acceptable medication dispensing package specifically contains fourth pills, capsules or other oral dosage forms comprising a dosage of 1000 mg/day of D-cycloserine for 18 days. In some embodiments, the pharmaceutically acceptable medication dispensing package specifically contains first, second, third and fourth pills as described according to this aspect.

In some embodiments, the pharmaceutically acceptable medication dispensing package is a blister pack, containing multiple discretely localized pills, capsules or other oral dosage forms, which differ in their content by desired groupings, for example, wherein the first pills, capsules or other oral dosage forms are in a part of a first row or a single row, or a row and an additional portion of a subsequent row, and contain a particular indicia, and the second pills, capsules or other oral dosage forms are grouped in a part of a subsequent row or within such row, or a row and an additional portion of a subsequent row, and contain a particular indicia, and to so forth, for each of the dosage forms contemplated.

In some embodiments, the pharmaceutically acceptable medication dispensing package is disposable.

In some embodiments, the pharmaceutically acceptable medication dispensing package comprises a second therapeutic agent for the treatment of depression retained and presented within a separate location in said package, and said second therapeutic agent is identified by visibly discernible indicia distinguishing the same from said first, second, third and fourth pills. Such second therapeutic agent may be any as described herein, and as will be appreciated by the skilled artisan.

In some embodiments, the pharmaceutically acceptable medication dispensing package comprises a second therapeutic agent at a dosage which is considered to be suboptimal for treating depression in said subject when treating said subject with said second therapeutic agent alone, as described hereinabove.

In some embodiments of the present invention, different sets of tablets, capsules or other oral dosage forms are disposed in different rows with each row being indicated by a successive week and each column being indicated as a different day of the week. In this embodiment, the sets of tablets having increased doses are disposed in receivers in rows indicated as successive dosage changes.

It will be appreciated that the formal disposition of the different dosages within the medication dispensing package may be according to any plan or pattern, for example, the dosage forms may be disposed in different columns, with each column or successive part thereof being indicated as a successive dosage, while each row, for example, may indicate a particular day of the week.

In another embodiment of the present invention, the medication dispensing package for enabling compliance with a regimen of changing doses of medication over a period of time includes a backing having an array or receivers with the array including a plurality of columns and a plurality of rows. In this embodiment, a plurality of sets of tablets are provided with each set being disposed in receivers of a plurality of adjacent rows or a plurality of adjacent columns. This plurality may be two and each tablet in a set has a common dose of medication and a different dose than a tablet or other oral dosage form in a different set.

In some embodiments, according to this aspect, pairs of adjacent rows may have differing sets of oral dosage forms, for example, allowing for the change of dosage over a several-week period of time from the various dosages or ranges of dosages presented herein.

In some embodiments, the pharmaceutical compositions can be administered to the to patient by any, or a combination, of several routes, for example, whereas D-cycloserine may be administered orally, the second therapeutic agent administered, as herein described may be administered by any appropriate route, for example, such second therapeutic agent may be provided as an oral, intravenous, trans-mucosal (e.g. nasal, vaginal, etc.), pulmonary, transdermal, ocular, buccal, sublingual, intraperitoneal, intrathecal, intramuscular, or long term depot preparation.

In some embodiments, this invention contemplates compositions containing both D-cycloserine and a at a therapeutic agent for the treatment of depression, suicide or suicide ideation in a subject, where the composition is formulated to provide an oral daily dosage of from about 500 mg/day-1200 mg/day In some embodiments, solid compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, lipids, alginic acid, or ingredients for controlled slow release. Disintegrators that can be used include, without limitation, micro-crystalline cellulose, corn starch, sodium starch glycolate and alginic acid. Tablet binders that may be used include, without limitation, acacia, methylcellulose, sodium carboxymethylcellulose, polyvinylpyrrolidone (Povidone), hydroxypropyl methylcellulose, sucrose, starch, and ethylcellulose.

In some embodiments, liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the patient to be treated.

In some embodiments, the second therapeutic agent may be formulated as an injectable composition, which may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like).

In some embodiments, the second therapeutic agent may be formulated as an intravenous injection, the compounds may be administered by the drip method, whereby a pharmaceutical composition containing the active compound(s) and a physiologically acceptable excipient is infused.

Physiologically acceptable excipients may include, for example, 5% dextrose, to 0.9% saline, Ringer's solution or other suitable excipients. For intramuscular preparations, a sterile composition of a suitable soluble salt form of the compound can be dissolved and administered in a pharmaceutical excipient such as Water-for-Injection, 0.9% saline, or 5% glucose solution, or depot forms of the compounds (e.g., decanoate, palmitate, undecylenic, enanthate) can be dissolved in sesame oil. Alternatively, the pharmaceutical composition can be formulated as a chewing gum, lollipop, or the like.

While the dosage regimen and methods described herein represent an optimum arrived at by administering the D-cycloserine orally, it will be appreciated by the skilled artisan that a lower dosage may be accomplished with the same by administering the D-cycloserine by a route that does not undergo first pass metabolism. According to this aspect, the dosage can be adjusted to be staggered accordingly, as presented for the oral dosage regimens described herein, with proportionately lower dosages, to accommodate a non-oral administration route, and such alterations are to be considered to be an embodied regimen of this invention.

In other embodiments, the formulations as herein described, in particular with regard to oral formulations, are envisioned to comprise slow release tablet formulations. Such slow release tablet formulations may, for example, comprise commercially available formulations containing known anti-depressant medications, such as, for example, Effexor® or Seroquel®, both of which are already available in extended length (XR) formulations, however the formulation may be modified to further incorporate D-cycloserine.

In other embodiments, the formulations as herein described, in particular with regard to oral formulations, are envisioned to comprise both short acting and extended release formulations. Extended release formulations have the advantage inter alia of minimizing the difference between peak and trough levels of drug, and thereby to increase effectiveness and/or reduce side effects of a medication.

Methods for the formulation of the described regimens herein are well known, and the skilled artisan will appreciate that it is straightforward to prepare the oral dosage regimens as herein described. Applicants, for example, refer to Gibaldi's Drug Delivery Systems in Pharmaceutical Care, Desai A & Lee M (eds), Bethesda, Md.: American Society of Health-System Pharmacists, 2007.

D-cycloserine has a relatively short half-life in man, and therefore is presently used in BID dosing. In some embodiments of the invention BID dosing is envisioned. According to this aspect, and in some embodiments, such consideration will nonetheless ensure that the daily dosage described for the regimens defined herein are not exceeded.

In some embodiments of the invention, D-cycloserine is microencapsulated to increase its circulating half-life. According to this aspect, and in some embodiments, the microencapsulated compound would then be combined either with a anti-depressant medication that is already administered once daily (e.g. sertraline, citalopram, aripiprazole) to insure that cycloserine cannot be taken without accompanying antidepressant (which would increase risk of CNS side effects). Alternatively, the drug could be combined with an anti-depressant compound that is already typically given in divided doses (e.g. venlafaxine, quetiapine) and the two drugs could then be microencapsulated in common to yield a once-daily formulation with similar half-life between the two ingredients. Microencapsulation using standard approaches for (cf. Doshi DH, Oral Drug Delivery Systems, in Gibaldi's Drug Delivery Systems in Pharmaceutical Care, Desai A & Lee M (eds), Bethesda, Md.: American Society of Health-System Pharmacists, 2007. pp. 23-43) such as use of coating materials or matrix-based oral delivery systems. In one approach, for example, drugs are mixed with a gelling agent, such as hydroxypropylmethylcellulose or hydroxylpropylcellulose, which form a hydrophilic matrix (gel) upon contact with water that delays release of the compound. Release properties can be regulated by selection of specific gelling agents, as is known in the art (see, for example, U.S. Pat. No. 5,948,437; European patent EP20040765928, U.S. Pat. No. 7,807,195).

Other compounds that can be used to control release include cellulose, ethylcellulose, gelatin, hypromellose, iron oxide and titanium oxide. In some matrix systems, drug release is controlled mainly by diffusion through matrix pores and not by the erosion of the polymers. Drug delivery can also be controlled by use of reservoir type systems in which release is controlled by osmotic gradient across the coating membrane. Capsules can be manufactured which contain granules with different microencapsulation properties which can be blended to achieve a composition that has a desired release rate.

In one embodiment of the invention, D-cycloserine is microencapsulated along with quetiapine or a pharmaceutically acceptable salt thereof using a gelling agent such as hydroxypropyl methylcellulose, together with one or more pharmaceutically acceptable excipients. In some embodiments, the sustained release formulation comprises a hydrophilic matrix comprising a gelling agent, preferably hydroxypropyl methylcellulose, D-cycloserine, quetiapine and pharmaceutically acceptable salts thereof, together with one or more pharmaceutically acceptable excipients.

In another embodiment of the invention, D-cycloserine would be combined with venlafaxine formulated for extended release capsules (see patent EP 0797991, fully incorporated to herein by reference). In this embodiment, D-cycloserine and venlafaxine would be formulated to produce an extended release formulation by addition of hydroxypropylmethylcellulose to produce spheroids containing the active ingredients D-cycloserine and venlafaxine and then costed with a film coating to further delay release and/or extend the release profile. Concentrations of active ingredients, HPMC, film coatings and other excipients could be adjusted to produce the desired extended relief profile. For example, spheroids could contain from about 0.3-0.6% HPMC and coating levels could contain from about 6-8% film coating. Microcrystalline cellulose may be used instead of HPMC as described in EP 0797991, fully incorporated herein by reference.

In another embodiment of the invention, D-cycloserine would be combined with venlafaxine formulated for extended release tablets (see patent EP20040765928, fully incorporated herein by reference). In such embodiment, coboxyvinyl polymer is used as agent for formulation of tablets along with D-cycloserine and venlafaxine, with caboxyvinyl comprising about 8%-about 40% w/w of the tablet, most preferably from about 10-20%. Other rate controlling excipients for example hydrophilic matrices such as HPMC or hydrophobic matrices such as ethyl cellulose, waxes or fats, may be used in conjunction with carboxy vinyl polymer, in which case the amount of carboxy vinyl polymer may be reduced from the values above. A functional coating, for example an enteric coat or delay coat, may be applied to the tablet to delay and/or extend the release profile of the active D-cycloserine and anti-depressant ingredients. Carboxyvinyl polymers and coating agents are commercially available with preferential utility of Eudragit RS30D, Eudragit RL30D and Carbopol 971P (B.F. Goodrich, Cleveland, Ohio) as described in EP20040765928, fully incorporated herein by reference.

For delayed release formulation, ideal choice, concentration and composition of gelling agent, functional coatings or other ingredient can be determined by use of simulated gastrointestinal fluids to produce a formulation with prolonged release of D-cycloserine and second anti-depressant agent such as venlafaxine or quetiapine to produce a formulation with an extended relief profile of >8 hr, preferably 8-24 hr.

In some embodiments, the invention provides a method for treating depression in a subject, said method comprising orally administering D-cycloserine to a subject, wherein said D-cycloserine is administered in a dosage regimen as follows a first dosage of 50-300 mg/day of D-cycloserine for from 1 to 5 days, followed by:
    a second dosage of 300-600 mg/day of D-cycloserine for from 5 to 20 days, followed by:
    a third dosage of from 600-800 mg/day of D-cycloserine for from 21 days to 28 days, followed by:
    a fourth dosage of from 800-1200 mg/day of D-cycloserine for from day 29-43.

In some embodiments, the invention provides for the use of D-cycloserine in the preparation of a medicament or kit, formulated to provide a dosage regimen as follows a first dosage of 50-300 mg/day of D-cycloserine for from 1 to 5 days, followed by:
a second dosage of 300-600 mg/day of D-cycloserine for from 5 to 20 days, followed by:
a third dosage of from 600-800 mg/day of D-cycloserine for from 21 days to 28 days, followed by:
a fourth dosage of from 800-1200 mg/day of D-cycloserine for from day 29-43; for treating depression in a subject, wherein said D-cycloserine is formulated for oral administration to a subject.

In some embodiments, according to this aspect, the first dosage comprises 250 mg/day of D-cycloserine for 3 days, and in some embodiments, the second dosage comprises 500 mg/day of D-cycloserine for 18 days and in some embodiments, the third dosage comprises 750 mg/day of D-cycloserine for 7 days and in some embodiments, the fourth dosage comprises 1000 mg/day of D-cycloserine for 18 days, and in some embodiments, the first, second, third and fourth dosage comprise that described in accordance with this aspect.

In some embodiments, the method further comprises administering a second therapeutic agent for the treatment of depression to said subject. In some embodiments, the medicaments in accordance with the described uses of this invention further comprises a second therapeutic agent for the treatment of depression in said subject.

According to this aspect, the method is not limited in terms of the timing of the administration of the second therapeutic agent, such that the methods of this invention contemplate a subject already treated with a second therapeutic agent, or a naïve subject concomitantly treated with D-cycloserine and the second therapeutic agent, or in some embodiments, the subject initially treated with D-cycloserine is then administered a second therapeutic agent, and each of these scenarios represents an embodiment of this invention. Such second therapeutic agent will be any such agent as herein described, including a tetracyclic antidepressant (TeCA), selective serotonin reuptake inhibitor (SSRI), a serotonin/norephinephrine reuptake inhibitor (SNRI), an antipsychotic approved for treatment of depression or a combination thereof.

In some embodiments, in accordance with the methods/uses of this invention, the regimen comprises administering a second therapeutic agent at a dosage which is considered to to be suboptimal for treating depression in said subject when treating said subject with said second therapeutic agent alone.

In some embodiments, the invention provides a method for reducing the incidence or treating suicide or suicide ideation in a subject or population, said method comprising orally administering D-cycloserine to a subject, wherein said D-cycloserine is administered in a dosage regimen as follows
a first dosage of 50-300 mg/day of D-cycloserine for from 1 to 5 days, followed by:
a second dosage of 300-600 mg/day of D-cycloserine for from 5 to 20 days, followed by:
a third dosage of from 600-800 mg/day of D-cycloserine for from 21 days to 28 days, followed by:
a fourth dosage of from 800-1200 mg/day of D-cycloserine for from 29 days to 43 days.

In some embodiments, the invention provides for the use of D-cycloserine for the preparation of a medicament/kit formulated to provide a dosage regimen as follows
a first dosage of 50-300 mg/day of D-cycloserine for from 1 to 5 days, followed by:
a second dosage of 300-600 mg/day of D-cycloserine for from 5 to 20 days, followed by:
a third dosage of from 600-800 mg/day of D-cycloserine for from 21 days to 28 days, followed by:
a fourth dosage of from 800-1200 mg/day of D-cycloserine for from 29 days to 43 days for reducing the incidence or treating suicide or suicide ideation in a subject or population, wherein said D-cycloserine is formulated for oral administration.

In some embodiments, according to this aspect, the first dosage comprises 250 mg/day of D-cycloserine for 3 days, and in some embodiments, the second dosage comprises 500 mg/day of D-cycloserine for 18 days and in some embodiments, the third dosage comprises 750 mg/day of D-cycloserine for 7 days and in some embodiments, the fourth dosage comprises 1000 mg/day of D-cycloserine for 18 days, and in some embodiments, the first, second, third and fourth dosage comprise that described in accordance with this aspect.

In some embodiments, the method further comprises administering a second therapeutic agent for reducing the incidence or treating suicide or suicide ideation in a subject or population. In some embodiments, the medicaments in accordance with the described uses of this invention further comprises a second therapeutic agent for reducing the incidence or treating suicide or suicide ideation in a subject or population.

According to this aspect, the method is not limited in terms of the timing of the to administration of the second therapeutic agent, such that the methods of this invention contemplate a subject or population already treated with a second therapeutic agent, or a naïve subject or population concomitantly treated with D-cycloserine and the second therapeutic agent, or in some embodiments, the subject or population is initially treated with D-cycloserine and then administered a second therapeutic agent, and each of these scenarios represents an embodiment of this invention. Such second therapeutic agent will be any such agent as herein described, including a tetracyclic antidepressant (TeCA), selective serotonin reuptake inhibitor (SSRI), a serotonin/norephinephrine reuptake inhibitor (SNRI), an antipsychotic approved for reducing the incidence or treating suicide or suicide ideation in a subject or population or a combination thereof.

In some embodiments, in accordance with the methods of this invention, the regimen comprises administering a second therapeutic agent at a dosage which is considered to be suboptimal for reducing the incidence or treating suicide or suicide ideation in a subject or population when treating said subject with said second therapeutic agent alone.

Guilt is a known surrogate marker for suicide, and as is demonstrated hereinbelow, a significantly greater (p=0.01) reduction in guilt was observed in patients administered D-cycloserine versus patients receiving placebo alone.

The present invention also contemplates that the methods of this invention for treating/reducing the incidence of depression and/or suicide are also suitable, in particular, in a population exhibiting a minor allelic expression pattern for the GLDC gene consistent with a treatment resistant depression population. As described hereinbelow, a number of the participants exhibited a genotype distribution consistent with the elevated minor allele frequency in treatment resistant depression, and such subjects were responsive to the therapeutic regimen administered.

Thus the invention specifically contemplates, as certain embodiments of the same, that the methods and uses as herein described may be specifically for a subject or population having a genetic predilection to treatment-resistant depression.

In some embodiments, in accordance with the methods of this invention, the subject is provided with a pharmaceutically acceptable medication dispensing package as herein described as part of the therapeutic method.

As described in Textbook of INTERNAL MEDICINE, Kelley, et al. (eds.), Part X: Neurology, Chapter 469: Major Psychiatric Disorders, (J. Lippincott Co., Philadelphia), pp. 2198-2199 (1992), depression can occur throughout life and is at least twice as common in women as in men. Patients often present without the subjective sense of being depressed but complaining of somatic symptoms of depression, most commonly fatigue, sleep disturbances, or impotence. Patients may describe feeling sad, blue, low, irritable, or anxious, as well as being depressed. Diagnosis of major depression is based either on a distinct change of mood that is prominent, generally persists throughout the day, and occurs each day for at least 2 weeks or on markedly diminished interest or pleasure in most activities over a similar period. The diagnosis requires that at least four of the following symptoms be present nearly every day for a period of 2 weeks: significant weight loss (or weight gain in some younger patients), prominent sleep disturbance, agitation or retardation with slow speech, fatigue, feelings of worthlessness and guilt, slowed thinking, and hopelessness.

Depression can likewise be associated with the symptoms of disease (e.g., systemic lupus erythematosus) or as a side effect of the treatment of disease (e.g., with antihypertensive therapy). One form of depression, postpartum depression, has been commonly found in women during the period following childbirth.

The methods and materials of this invention are therefore suitable for treatment of depression or symptoms of depression associated with other diseases, as herein described.

Human clinical trials for the treatment of depression are well known in the art, preferably in blinded studies evaluating subjects provided with blinded samples of the test active agent or placebo, and as described below in the Examples.

Surprisingly, Applicants found highly beneficial treatment results when a dosage of 1000 mg/day was administered to the subjects. Accordingly, in one embodiment, this invention also provides a pharmaceutical composition comprising D-cycloserine formulated for oral administration providing a dosage of 1000 mg/day.

According to this aspect, and in one embodiment, the invention provides a method for the treatment of depression in a subject, said method comprising orally administering 1000 mg/day of D-cycloserine to a subject in need thereof, wherein said subject has first been administered D-cycloserine at dosage of between 50-500 mg/day of D-cycloserine for from 7 days to 21 says prior to administering said 1000 mg/day or D-cycloserine.

In some embodiments, according to this aspect, the subject has previously been administered or is concurrently administered a second therapeutic agent for the treatment of depression.

In some embodiments, according to this aspect, the second therapeutic agent comprises any such agent as herein described, for example, a tetracyclic antidepressant (TeCA), selective serotonin reuptake inhibitor (SSRI), a serotonin/norephinephrine reuptake inhibitor (SNRI), an to antipsychotic approved for use in treatment of depression or a combination thereof.

In some embodiments, according to this aspect, the second therapeutic agent is administered at a dosage, which is considered to be suboptimal for treating depression in said subject when treating said subject with said second therapeutic agent alone.

In some embodiments, according to this aspect, the invention further provides for the use of D-cycloserine in the preparation of a medicament formulated for oral administration at a dosage of 1000 mg/day for the treatment of depression in a subject in need thereof.

A subject undergoing treatment with the methods of the invention can experience significant improvements in depression. Relative to subjects treated with alternative treatments for depression, subjects treated according to the methods of the invention will experience, in some embodiments, greater improvement, or more long-lasting improvement, as measured by any clinically recognized assessment method for depression (e.g., the 21-item Hamilton Depression Rating Scale). It should be noted that not every subject will benefit from the methods of the invention, just as other pharmaceutical agents do not typically benefit every patient.

The following examples describe certain embodiments of the invention and should not be construed as limiting the scope of what is encompassed by the invention in any way.

EXAMPLES

Example 1

Beneficial Effects of D-Cyloserine on Major Depressive Symptoms in Treatment-Resistant Depression Methods This study was approved by the appropriate institutional review boards. Twenty-six patients meeting DSM-IV (Papp, M. and E. Moryl, Eur J Pharmacol, 1996. 316(2-3): p. 145-51) criteria for major depressive disorder and who were free of significant or unstable medical illness were enrolled in the study. Diagnosis was established on the basis of semi-structured psychiatric interviews, review of all available medical records and confirmation by two board-certified psychiatrists. All of the patients were poorly responsive to treatment with antidepressant drugs and have been receiving a stable therapeutic dose of an approved antidepressant drug for at least 8 weeks before study entry, i.e. all patients met criteria for refractory depression, defined as a >20 score on the 21-item HAM-D, despite at least 2 prior adequate antidepressant medications (e.g. SSRIs, SNRIs, TCAs) trials during the current depression episode. Ongoing medication doses remained fixed throughout the study.

After complete description of the study, orally and in writing, written, informed consent was obtained from all participating patients. A random assignment, double-blind placebo-controlled, parallel group design was used in the study. After a 2 wk (week −2 to baseline) assessment period, subjects were randomly allocated to receive under double blind conditions either D-cycloserine or placebo for 6 wk. D-cycloserine or placebo were given in addition to each patient's regular antidepressant medication, the dose of which remained fixed throughout the study. D-cycloserine and placebo were administrated orally, in identical capsules, and according to the same dose escalation schedule. Plasma glycine and serine levels were determined pre/post treatment for a subgroup of 20 subjects by HPLC. Results were compared to those of normal comparison subjects drawn from a previous study of glycine levels in schizophrenia patients vs. controls using a demographically similar population (Neeman et al., 2004)

A fixed, slow titration-high dose treatment schedule for adjuvant treatment with D-cycloserine was conceptualized and used with all participating patients during the 6 wk study period: 250 mg/day for 3 days ◊ 500 mg/day for 18 days ◊ 750 mg/day for one week ◊ 1000 mg/day (1 g/day) for two weeks.

Several scales were used throughout the study to assess the severity of symptoms and side effects in each patient. All the assessments were performed by a psychiatrist who was blind to the experimental treatment assignment. HAM-D (1) was used at wk. −2, baseline and bi-weekly throughout the study. HAM-A (3), BDI (2) and the Clinical Global Impression—Severity of Illness Scale (31) were used at baseline and biweekly throughout the study. In addition to the symptoms sensitive to psychosis development that are included in HAM-D, overall side effects were assessed at baseline and biweekly throughout the study using the UKU side effects rating scale for the registration of unwanted effects of psychotropic drugs (32) BDI scores were available only for 20 of the 26 study participants.

Primary data analysis was conducted by mixed-model regression using all available data. Subject id was coded as index variable, treatment week (0-6) as repeated measure, and treatment as fixed factor. A secondary analysis assessed effect size of change scores from baseline to end of treatment based upon LOCF measures for all subjects. Significance of change across treatment week was evaluated using repeated measures ANOVA. Follow-up t-tests were performed to evaluate differential response by older (TCA) vs. newer (TeCA, SSRI/SSRI) treatment.

Results

The demographic and clinical characteristics of the 26 patients that participated in the study are summarized in Table 1.

TABLE 1

Demographic and Clinical Characteristics of the Sample*

|  | D-Cycloserine (N = 13) | Placebo (N = 13) | Total sample (N = 26) |
|---|---|---|---|
| Age, y. | 52.8 ± 11.5 | 53.1 ± 9.4 | 53.0 ± 10.2 |
| Male/Female | 5/8 | 5/8 | 10/16 |
| Marital status (Married/Divorced/Widowed) | 10/2/1 | 11/2/— | 21/4/1 |
| Length of illnes, y. | 16.8 ± 14.6 | 12.6 ± 15.7 | 14.4 ± 14.4 |
| Number of previous episodes | 3.3 ± 1.0 | 2.8 ± 1.2 | 3.0 ± 1.1 |
| Duration of current episode, mo. | 14.0 ± 17.1 | 12.3 ± 12.4 | 13.2 ± 14.3 |
| Baseline rating scale scores |  |  |  |
| HAM-D | 25.1 ± 5.6 | 27.2 ± 4.9 | 26.2 ± 5.4 |
| HAM-A | 27.6 ± 6.7 | 26.7 ± 5.8 | 27.2 ± 6.4 |
| CGI-S | 5.2 ± 0.4 | 5.3 ± 0.6 | 5.3 ± 0.5 |
| BDI | 35.3 ± 8.3 | 35.3 ± 7.5 | 35.3 ± 7.6 |

*Values are mean ± SD for continuous variables and number of subjects for categorical values.
HAM-D, 21 Item - Hamilton Depression Rating Scale; HAM-A, Hamilton Rating Scale for Anxiety;
BDI, Beck Depression Inventory, Second Edition;
CGI-S, Clinical Global Impression - Severity of Illness Scale Patients were receiving the following medications, alone or in combination: mirtazapine (6), duloxetine (5), venlafaxine (4), escitalopram (2), citalopram (2), fluoxetine (1), paroxetine (1), mianserine (1), reboxitine (1), desipramine (1), clomipramine (1), imipramine (1), hypericum (1) clonazepam (3), low dose sulpiride (3), lorazepam (1), diazepam (1), oxazepam (1) and carbamazepine (1). The characteristics of patients randomized to receive D-cycloserine did not differ from those of patients randomized to receive placebo. For all subjects, depression symptoms, as reflected in HAM-D scores, were stable for at least 2 wk prior to experimental treatment initiation (Table 2).

TABLE 2

HAM-D Scores Prestudy and at Experimental Treatment Initiation

| HAM-D score | Initial Assignment | Prestudy (wk −2) | Initiation (baseline) |
|---|---|---|---|
| Total | D-cycloserine | 25.3 ± 4.1 | 25.1 ± 5.6 |
|  | Placebo | 24.4 ± 3.8 | 27.2 ± 4.9 |
| Guilt | D-cycloserine | 2.3 ± 0.6 | 1.5 ± 0.9 |
|  | Placebo | 1.5 ± 1 | 1.4 ± 0.9 |
| Depersonalization/ | D-cycloserine | 0.7 ± 0.6 | 0.3 ± 0.9 |
| Derealization | Placebo | 0.0 ± 0.0 | 0.0 ± 0.0 |
| Paranoia | D-cycloserine | 0.3 ± 0.5 | 0.1 ± 0.3 |
|  | Placebo | 0.0 ± 0.0 | 0.1 ± 0.3 |

*Values are mean ± SD. HAM-D, 21 item - Hamilton Depression Rating Scale

Thirteen patients were randomly allocated to receive adjuvant D-cycloserine treatment and thirteen patients were randomly allocated to receive adjuvant placebo. A total of twenty two patients, ten in the D-cycloserine group and twelve in the placebo group completed the entire study. Four patients were withdrawn from the study: one in the placebo group, due to complaints of chest pain, and three in the D-cycloserine group due to non-compliance, and complaints of ear aches and tiredness, respectively. Following withdrawal from the study, these complaints ceased. No other complaints were registered throughout the study and no D-cycloserine/placebo treatment side effects were noted using the UKU scale for rating side effects.

D-cycloserine treatment led to significant improvement in depressive symptoms as measured by HAM-D ($p=0.005$) and the BDI ($p=0.046$) (Table 3).

Comparison by glycine levels: Pre-treatment plasma glycine levels for the depression group as a whole (371.9±160.9 $\mu$M) were significantly greater than those observed in age-matched normal comparison subjects (244.8±84.2 $\mu$M, $p=0.002$). Glycine levels post-treatment (339.0±97.3 $\mu$M) were not significantly different from pre-treatment levels. A cutoff level of 300 $\mu$M significantly distinguished groups (Fisher exact test $p=0.001$).

When HAM-D change scores were analyzed as a function of pretreatment glycine levels, including glycine <300 $\mu$M vs. ≥300 $\mu$M as a factor led to a significant treatment X glycine level interaction ($p=0.043$). Effect size vs. placebo among patients with pretreatment glycine ≥300 $\mu$M (n=14) was extremely large (d=2.36), suggesting robust antidepressant effects. Similarly, 4 of 7 (57%) patients with pre-treatment glycine levels ≥300 $\mu$M were remitters vs. only 1 of 5 (20%) of non-remitters, suggesting that patients with elevated pretreatment glycine levels show unexpected and particular sensitivity to glycine antagonist treatment.

TABLE 3

Symptom levels by treatment and week (mean ± SD)

| Outcome measure HAM-D | Treatment | Baseline | Week 2 | Week 4 | Week 6 | LOCF | $F^1$ | df | p | d |
|---|---|---|---|---|---|---|---|---|---|---|
| Total | D-cycloserine | 25.1 ± 5.6 | 17.8 ± 8.1 | 15.4 ± 10.9 | 11.6 ± 10.0 | 13.1 ± 9.4 | 8.49 | 1,80.7 | 0.005 | 0.91 |
|  | Placebo | 27.2 ± 4.9 | 22.8 ± 7.4 | 22.4 ± 6.9 | 21.5 ± 8.7 | 23.3 ± 9.6 |  |  |  |  |
| Guilt | D-cycloserine | 1.5 ± .9 | 1.1 ± 1.0 | 0.9 ± 1.0 | 0.4 ± .7 | 0.5 ± 0.8 | 0.32 | 1,93.9 | 0.6 | 0.89 |
|  | Placebo | 1.4 ± .9 | 1.2 ± .9 | 1.0 ± .9 | 0.9 ± .9 | 1.1 ± 1.0 |  |  |  |  |
| Depersonalization/ Derealization | D-cycloserine | 0.3 ± 0.9 | 0.1 ± 0.3 | 0.0 ± 0.0 | 0.0 ± 0.0 | 0.0 ± 0.0 | — | — | — | 0.72 |
|  | Placebo | 0.0 ± 0.0 | 0.0 ± 0.0 | 0.0 ± 0.0 | 0.0 ± 0.0 | 0.0 ± 0.0 |  |  |  |  |
| Paranoia | D-cycloserine | 0.1 ± .3 | 0.2 ± .4 | 0.2 ± .4 | 0.1 ± 0.3 | 0.2 ± 0.4 | 2.54 | 1,85.3 | 0.12 | −0.31 |
|  | Placebo | 0.1 ± .3 | 0.1 ± .3 | 0.0 ± .0 | 0.0 ± 0.0 | 0.1 ± 0.3 |  |  |  |  |
| HAM-A | D-cycloserine | 27.6 ± 6.7 | 19.0 ± 9.9 | 16.8 ± 10.0 | 12.2 ± 10.1 | 14.2 ± 9.8 | 3.27 | 1,89.2 | 0.074 | 0.85 |
|  | Placebo | 26.7 ± 5.8 | 22.7 ± 7.2 | 21.1 ± 4.9 | 19.5 ± 5.8 | 21.0 ± 7.9 |  |  |  |  |
| CGI-S | D-cycloserine | 5.2 ± 0.4 | 4.5 ± 0.9 | 3.8 ± 1.5 | 3.0 ± 1.7 | 3.4 ± 1.7 | 4.01 | 1,50.2 | 0.051 | 0.99 |
|  | Placebo | 5.3 ± 0.6 | 4.9 ± 0.8 | 4.9 ± 1.1 | 5.0 ± 0.8 | 4.8 ± 1.2 |  |  |  |  |
| BDI | D-cycloserine | 35.3 ± 8.3 | 28.3 ± 10.5 | 22.9 ± 13.2 | 18.4 ± 14.2 | 20.0 ± 14.1 | 4.13 | 1,71.7 | 0.046 | 0.95 |
|  | Placebo | 35.3 ± 7.5 | 29.6 ± 6.7 | 30.3 ± 6.1 | 27.9 ± 7.3 | 31.1 ± 9.9 |  |  |  |  |

[1]Mixed model regression

Trends toward improvement were observed as well for anxiety, as reflected in the HAM-A (p=0.051) and overall level of function, as reflected in the CGI-S (p=0.076). No significant change was observed in items potentially reflecting psychosis, including depersonalization/derealization and paranoia, which remained negligible in both treatment groups throughout the study.

Only one subject in the study (D-cycloserine group) had significant suicidal ideation on study entry, as reflected in HAM-D suicide item (item 3)>2. In this subject, symptoms resolved within two weeks and remained reduced throughout the remainder of the study. No significant effect on guilt feelings was observed in the primary analysis. Nevertheless a significantly greater to (p=0.01) reduction in guilt was observed in a completers analysis, with patients on D-cycloserine (n=10) showing a 1.3±0.5 pt reduction in guilt feelings vs. 0.4±0.9 in patients on placebo (n=11), also suggesting reduced suicide risk.

Responders analysis: Categorical analyses were conducted for responders, defined as 50% or greater reduction in HAM-D symptoms, and remitters, defined as HAM-D≤7. Seven of 13 (54%) patients assigned to D-cycloserine qualified as responders vs. 2 of 13 (15%) assigned to placebo ($\chi^2$=4.24, df=1, p=0.039). Five of 13 (38%) patients assigned to D-cycloserine also were considered remitters vs. 2 of 13 (15%) assigned to placebo, although this difference was not statistically significant ($\chi^2$=1.76, df=1, p=0.19).

| TCA (n = 2) Outcome Measure | TCA (n = 2) | | SSRI/SNRI/TeCA (n = 11) | | T | df | p |
|---|---|---|---|---|---|---|---|
|  | mean | sd | mean | sd |  |  |  |
| % Responder | 0.0 | 0.0 | 63.6 | 50.4 | 4.18 | 10.0 | 0.002 |
| % Remitter | 0.0 | 0.0 | 45.5 | 52.2 | 2.89 | 10.0 | 0.016 |
| HAM-D (baseline) | 25.5 | 3.5 | 25.0 | 6.1 | .16 | 2.3 | .9 |
| HAM-D (LOCF) | 22.5 | 0.7 | 11.4 | 9.2 | 3.94 | 10.5 | .002 |

Comparison by antidepressant type: Of the 13 patients randomized to active treatment, 11 were being treated with newer antidepressants including SSRIs/SNRIs or TeCAs, and 2 with TCAs. Comparison of response between patients receiving older vs. newer antidepressants showed a significantly higher response and remission rate among those receiving newer antidepressants, as well as a between-group difference in depressive symptoms at week 21 using the HAM-D. In addition, both of the patients receiving TCAs (100%) showed non-zero psychosis scores a week 6, vs. 5 of 10 receiving newer antidepressants (50%). However, no subjects were discontinued from either group because of psychotic symptoms.

Genotype information for the rs10975641 locus of the GLDC enzyme was obtained for 7 of the participants in the active treatment arm. Genotype distribution was 1:3:3 for CC, CG, and GG genotypes, respectively, yielding minor allele (G) frequency of 0.64. This is consistent with the elevated minor allele frequency in treatment resistant depression observed by Ji et al. (2010). Among the 6 patients with minor allele (G), there was a 15.2±8.2 pt reduction in HAM-D symptoms vs. 3.8±9.8 pts in the placebo group (p=0.025). Furthermore, 5/6 were responders (83.3%) vs. 2/13 (15%) in the placebo group (p=0.002).

The present study is the first to demonstrate antidepressant effects of D-cycloserine or other glycine site antagonists in combination with antidepressants. Furthermore, they to demonstrate that such agents are particularly effective when used with newer antidepressants such as TeCAs and SSRIs/SNRIs, which appear to have sufficient intrinsic antipsychotic efficacy to prevent psychotic reactions observed in earlier studies of high dose D-cycloserine in depression, and particularly effective in depressed patients with elevated pretreatment plasma glycine levels. The present study provides for the unexpected finding that the newer antidepressants such as TeCAs and SSRIs/SNRIs were sufficient to prevent psychotic symptoms, while not interfering with the anti-deperessant response of the same.

In addition, this is the first study to test DCS in patients diagnosed with major depressive disorder according to modern (DSM-IV) criteria. The ability of newer antidepressants to prevent psychotic reactions reported in prior studies with D-cycloserine in depression suggests that combination treatments with newer antidepressants may be particularly effective. In addition, many antipsychotic agents such as quetiapine, risperidone and olanzapine are indicated in treatment of depression. A combination of D-cycloserine and an antipsychotic would therefore constitute another embodiment of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

All publications, patents, and patent applications mentioned herein are hereby incorporated by reference in their entirety as if each individual publication or patent was specifically and individually indicated to be incorporated by reference. In case of a conflict between the specification and an incorporated reference, the specification shall control. Where number ranges are given in this document, endpoints are included within the range. Furthermore, it is to be understood that unless otherwise indicated or otherwise evident from the context and understanding of one of ordinary skill in the art, values that are expressed as ranges can assume any specific value or subrange within the stated ranges, optionally including or excluding either or both endpoints, in different embodiments of the invention, to the tenth of the unit of the lower to limit of the range, unless the context clearly dictates otherwise. Where a percentage is recited in reference to a value that intrinsically has units that are whole numbers, any resulting fraction may be rounded to the nearest whole number.

In the claims articles such as "a,", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. A method of treating treatment-refractory depression, comprising: administering D-cylcoserine at a dosage of 1000 mg/day-2000 mg/day to a patient under treatment for depression wherein said patient is receiving either an approved antidepressant agent selected from the group consisting of tetracyclic antidepressants (TeCA), selective serotine reuptake inhibitors (SSRIs), and serotonin/norepinephrin reuptake inhibitors (SNRIs), or an antipsychotic agent approved for treatment of depression, wherein said patient is treatment-refractory, and wherein said patient is experiencing side effects from receiving said antidepressant or said antipsychotic agent.

2. The method of claim 1, wherein said subject suffers from mania.

3. The method of claim 1, wherein said subject suffers from bipolar disorder.

4. The method of claim 1, wherein said anti-depressant agent is ketamine.

5. The method of claim 1, wherein said anti-depressant agent is an anti-NMDA agent.

6. The method of claim 1, wherein said subject possesses a polymorphism for a GLDC allele.

7. The method of claim 1, wherein said D-cycloserine is administered at a dosage of 1200 mg/day-2000 mg/day.

8. The method of claim 1 wherein either of said antidepressant or antipsychotic agent is administered at a dosage amount that is less than effective.

9. The method of claim 1 wherein the administration of said D-cycloserine and said antidepressant or antipsychotic agent is provided in a single pharmaceutical formulation.

10. The method of claim 1 wherein the administration of said D-cycloserine and said antidepressant or antipsychotic agent is provided as two separate pharmaceutical formulations.

11. The method of claim 1 wherein said D-cycloserine is administered separately with said antidepressant or antipsychotic agent.

12. A method of reducing the side effects of D-cycloserine in a human comprising:
    administering D-cylcoserine at a dosage of 1000 mg/day-2000 mg/day together with an effective amount of either an approved antidepressant agent selected from the group consisting of tetracyclic antidepressants (TeCA), selective serotonin reuptake inhibitors (SSRIs), and serotonin/norepinephrin reuptake inhibitors (SNRIs), or an antipsychotic agent approved for treatment of depression to a patient, wherein said patient is refractory to treatment of depression.

* * * * *